US011071499B2

(12) United States Patent
Durand et al.

(10) Patent No.: US 11,071,499 B2
(45) Date of Patent: Jul. 27, 2021

(54) MULTICHANNEL ULTRA-LOW NOISE AMPLIFIER

(71) Applicant: Case Western Reserve University, Cleveland, OH (US)

(72) Inventors: Dominique M. Durand, Solon, OH (US); Yazan M. Dweiri, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 566 days.

(21) Appl. No.: 15/185,183

(22) Filed: Jun. 17, 2016

(65) Prior Publication Data

US 2017/0332973 A1    Nov. 23, 2017

Related U.S. Application Data

(60) Provisional application No. 62/337,445, filed on May 17, 2016.

(51) Int. Cl.
*A61B 5/00* (2006.01)
*H03F 3/45* (2006.01)
*A61B 5/24* (2021.01)

(52) U.S. Cl.
CPC ............ *A61B 5/7203* (2013.01); *A61B 5/24* (2021.01); *A61B 5/7225* (2013.01);
(Continued)

(58) Field of Classification Search
CPC ......... A61B 5/72; A61B 5/7203; A61B 5/721; A61B 5/04; A61B 5/04001; A61B 5/7225;
(Continued)

(56) References Cited

U.S. PATENT DOCUMENTS 5,382,956 A * 1/1995 Baumgartner ...... H03F 3/45188
341/155
5,467,090 A * 11/1995 Baumgartner ....... A61B 5/0428
341/155

(Continued)

OTHER PUBLICATIONS

Mesut Sahin, Musa A. Haxhiu, Dominique M. Durand, Ismail A. Dreshaj. "Spiral nerve cuff electrode for recordings of respiratory output." Journal of Applied Physiology Jul. 1997, 83 (1) 317-322.
(Continued)

*Primary Examiner* — Matthew Kremer
*Assistant Examiner* — Avery M Foley
(74) *Attorney, Agent, or Firm* — Tarolli, Sundheim, Covell & Tummino LLP (57) ABSTRACT

The present disclose generally relates to a multichannel low-noise amplifier. At each input to the multichannel low-noise amplifiers, a plurality of transistors can be connected in parallel. This parallel connection decreases the voltage noise beyond what is possible using a single input transistor at each input. As an additional benefit, the initial operating region of the input transistors is not changed. The multichannel low-noise amplifier can be incorporated on a single integrated circuit chip to amplify biological signals to facilitate selective recording of a property (e.g., amplifying neural signals to facilitate selective recording of neural activity).

5 Claims, 5 Drawing Sheets

(52) U.S. Cl.
CPC ...... *H03F 3/45183* (2013.01); *A61B 2503/40* (2013.01); *H03F 2200/261* (2013.01); *H03F 2200/294* (2013.01); *H03F 2203/45288* (2013.01); *H03F 2203/45322* (2013.01); *H03F 2203/45371* (2013.01)

(58) Field of Classification Search
CPC ..... A61B 5/7228; A61B 5/24; A61B 2503/40; H03F 3/45183; H03F 2200/261; H03F 2200/264; H03F 2200/27; H03F 2200/294; H03F 2203/45288; H03F 2203/45322; H03F 2203/45371; H03F 3/4521; H03F 3/45224; H03F 3/45251; H03F 2200/267; H03F 2200/306; H03F 2200/309; H03F 2200/303; H03F 2200/297; H03F 2200/366; H03F 2203/45296; H03F 2203/45358; H03F 2203/45361; H03F 2203/45362; H03F 2203/45364; H03F 2203/45366; H03F 2203/45368; H03F 2200/336
See application file for complete search history.

(56) References Cited

U.S. PATENT DOCUMENTS

| | | | | |
|---|---|---|---|---|
| 5,969,573 | A | * | 10/1999 | Koike ..................... H03F 1/303 330/253 |
| 9,148,087 | B1 | * | 9/2015 | Tajalli ................... H03F 1/0205 |
| 2006/0186951 | A1 | * | 8/2006 | Ohannaidh ........ H03H 11/1213 327/552 |
| 2010/0253433 | A1 | * | 10/2010 | Velasquez ........... H03F 3/45183 330/257 |
| 2011/0158435 | A1 | * | 6/2011 | Ono ...................... H03F 1/0261 381/120 |
| 2011/0234322 | A1 | * | 9/2011 | Bowers .................. H03F 1/302 330/296 |
| 2013/0147559 | A1 | * | 6/2013 | Schaffer ................. H03F 3/211 330/257 |
| 2017/0126185 | A1 | * | 5/2017 | Kang ..................... H03F 1/565 |

OTHER PUBLICATIONS

Harrison, Reid R. and Cameron Charles. "A low-power low-noise CMOS amplifier for neural recording applications." IEEE Journal of solid-state circuits 38.6 (2003): 958-965.

Poussart, Denis J-M. "Low-level average power measurements: noise figure improvements through parallel or series connection of noisy amplifiers." Review of Scientific Instruments 44.8 (1973): 1049-1052.

Wikswo, John P., Philip C. Samson, and Robin P. Giffard. "A low-noise low input impedance amplifier for magnetic measurements of nerve action currents." IEEE Transactions on Biomedical Engineering 4 (1983): 215-221.

Johns, David A., and Ken Martin. Analog integrated circuit design. John Wiley & Sons, 2008.

Seese, Timothy M., et al. "Characterization of tissue morphology, angiogenesis, and temperature in the adaptive response of muscle tissue to chronic heating." Laboratory investigation; a journal of technical methods and pathology 78.12 (1998): 1553-1562.

* cited by examiner

MULTICHANNEL ULTRA-LOW NOISE AMPLIFIER

CROSS-REFERENCE TO RELATED APPLICATIONS

This application claims the benefit of U.S. Provisional Application No. 62/337,445, entitled "MULTICHANNEL CMOS AMPLIFIER," filed May 17, 2016. The entirety of this provisional application is hereby incorporated by reference for all purposes.

GOVERNMENT FUNDING

This invention was made with government support under grant NS032845 awarded by the National Institutes of Health (NIH). The government has certain rights in the invention.

TECHNICAL FIELD

The present disclosure relates generally to a multichannel ultra-low noise amplifier and, more specifically, to the use of the multichannel ultra-low noise amplifier for biological recordings.

BACKGROUND

Recently, there has been a demand for specialized amplifier circuitry to facilitate detection of weak signals, like biological signals (e.g., neural signals) generated in biological applications. For example, the advent of multichannel amplifiers has enabled significant acceleration of advances in many biological applications, such as the creation of neural interfaces, which require a large number of channels. For use in such neural applications, the multichannel amplifier should provide low power consumption while minimizing noise added to the detected signal. For example, when implanted, such multi-channel amplifiers should reduce heat flux to the surrounding living tissue while being small enough to fit within a small size integrated circuit (IC) layout. Accordingly, there is a demand for technologies that possess the capacity to integrate a multi-channel low noise amplifier, which provides low power consumption, into a small IC layout.

SUMMARY

The present disclosure relates generally to a multichannel ultra-low noise amplifier and, more specifically, to the use of the multichannel ultra-low noise amplifier for biological recordings. The multichannel ultra-low noise amplifier can be embodied within a small integrated circuit (IC) layout while providing low power consumption to facilitate use in biological applications (e.g., to reduce heat flux to the surrounding living tissue).

In one aspect, the present disclosure can include an ultra-low noise amplifier. The ultra-low noise amplifier can include at least a differential input circuit, a current mirror circuit, and an output. The differential input circuit can include an inverting voltage input (V−) comprising a plurality of parallel transistors and a non-inverting voltage input (V+) comprising a mirrored plurality of parallel transistors. The current mirror circuit, coupled to drains of each of the parallel transistors, can be biased based on a number of the plurality of parallel transistors and a biasing current value. The output, coupled to the current mirror circuit, can provide an amplified output voltage based on a current difference between the plurality of parallel transistors and the mirrored plurality of parallel transistors.

In another aspect, the present disclosure can include a method for recording biological signals. The method can include receiving signals at inputs to an ultra-low noise amplifier. The inputs each comprise a plurality of parallel transistors. The method also includes amplifying the signals to facilitate selective recording of biological signals, such as signals indicating neural activity.

In a further aspect, the present disclosure can include an implantable device. The implantable device can include one or more recording electrodes. The implantable device can also include an ultra-low noise amplifier, coupled to the one or more recording electrodes. The ultra-low noise amplifier can include a differential input circuit comprising an inverting voltage input (V−) comprising a plurality of parallel transistors and a non-inverting voltage input (V+) comprising a mirrored plurality of parallel transistors.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "multichannel amplifier" can refer to an electronic device for increasing the amplitude of electrical signals having two or more input channels.

As used herein, the term "operational transconductance amplifier" or "OTA" can refer to an amplifier whose differential input voltage produces an amplified output voltage.

As used herein, the term "complimentary metal-oxide semiconductor" or "CMOS" can refer to a technology used to constrict integrated circuits. Two important characteristics of CMOS devices are (1) high noise immunity and (2) low static power consumption, As used herein, the term "transconductance" or "$g_m$" can refer to an electrical characteristic relating an output current to an input voltage. As an example, in a CMOS OTA, the transconductance can be proportional to the drain current ($I_D$).

As used herein, the term "parallel" can refer to a connection of two or more circuit components having an equivalent potential difference thereacross.

As used herein, the term "integrated circuit" or "IC" can refer to a set of electric circuits on one small plate or chip of semiconductor material (e.g., silicon).

As used herein, the term "biological recording" can refer to the acquisition of one or more signals produced by a living organism. For example, neural recording is a type of biological recording that refers to the acquisition of one or more neural signals produced by the nervous system (central nervous system or peripheral nervous system) of a living organism.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc. For example, the multichannel ultra-low noise amplifier can be used in the collection of biological recordings from a subject.

As used herein, the term "coupled" can refer to a physical (also referred to as "wired") connection between elements and/or a wireless connection between elements to facilitate transmission of data and/or signals.

II. Overview

The present disclosure relates generally to a multichannel ultra-low noise amplifier and, more specifically, to the use of the multichannel ultra-low noise amplifier for biological recordings (e.g., neural recordings). The multichannel ultra-low noise amplifier can be a high channel count and low power operational transconductance amplifier (OTA) that employs complimentary metal-oxide semiconductor (CMOS) technology. CMOS technology has long been an attractive solution because it provides an inherently low current noise, low power consumption, and small surface area, which enables the layout of the high channel count on a single silicon wafer; however, CMOS technology is limited due to high voltage noise.

One way to achieve the lowest possible voltage noise is by optimizing the geometry of the input transistor (width-to-length ratio) to increase the transconductance ($g_m$). However, the surface area of a single transistor cannot be arbitrarily increased in order to indefinitely increase $g_m$ due to the ratio between $g_m$ the and the drain current ($I_D$) being confined by an upper limit (approximately 27 V$^{-1}$). However, another way to achieve the lowest possible voltage noise, which is used by the multichannel ultra-low noise amplifier of the present disclosure, is by connecting a plurality of transistors in parallel at each input to increase the effective value of $g_m$ proportionally with the count of parallel input transistors and consequently to decrease the voltage noise beyond what is possible with the use of a single input transistor at each input. Another benefit of the multichannel ultra-low noise amplifier of the present disclosure is that the initial operating region of the input transistors is not changed since the same value of $g_m/I_D$ is used for the individual input transistors.

III. Systems

One aspect of the present disclosure can include a system 10 (FIG. 1) that can amplify recorded signals. The recorded signals, in some examples, can be biological signals (e.g., neural signals). Accordingly, the system 10 can be implantable to record such biological signals. In these instances, the system 10 can provide the benefits of a low noise, low power consumption design. Advantageously, the low noise operation can enable the user of system 10 to record and amplify biological signals of a low magnitude (e.g., ~20 µV p-p), while providing an acceptable signal-to-noise ratio, and the low power consumption can reduce heat flux to living tissue surrounding the system 10.

Figure 1:
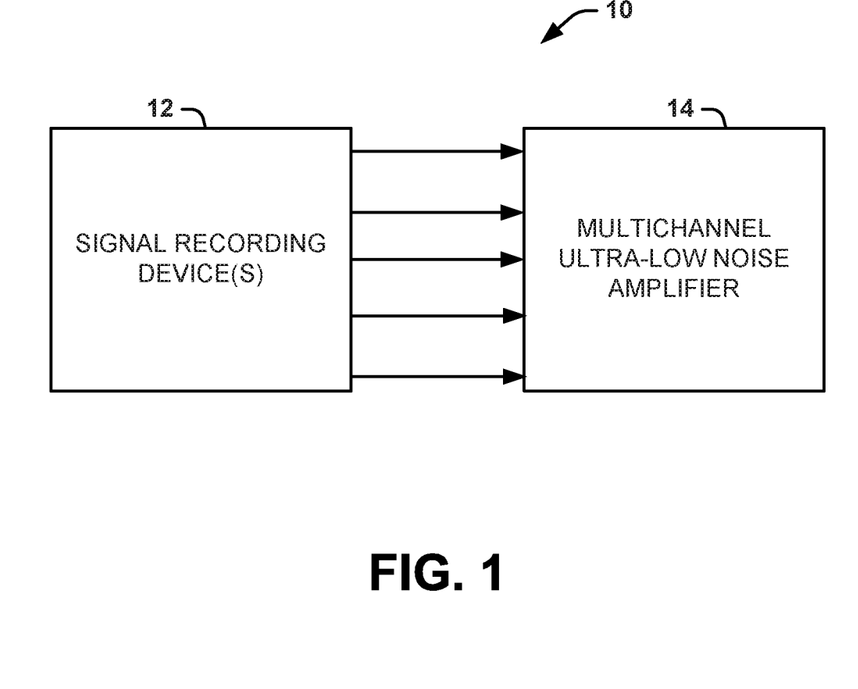
FIG. 1 is a block diagram showing a system that amplifies recorded signals using a multi-channel ultra-low noise amplifier in accordance with an aspect of the present disclosure.

The system 10 can include a signal recording device 12 coupled to an ultra-low noise amplifier 14. The coupling between the signal recording device 12 and the ultra-low noise amplifier can be a physical or wired connection and/or a wireless connection. The ultra-low noise amplifier can provide a signal with a higher amplitude for further processing. The further processing can be done by a device with computing or processing power (not shown), as an example. The ultra-low noise amplifier 14 can transmit the amplified signal to the device via a wired connection and/or a wireless connection.

In the simplest form, the system 10 can include a signal recording device 12 coupled to an ultra-low noise amplifier 14. As an example, the signal recording device 12 can include an electrode or an electrode contact. However, the signal recording device 12 can include one or more signal recording devices. In this case, the signal recording device 12, as an example, can include a plurality of electrodes or a plurality of electrode contacts. Additionally, the ultra-low noise amplifier 14 can be a multichannel ultra-low noise amplifier that receives inputs in different channels from the different signal recording devices. For example, in neural recordings, the multiple channels, advantageously, can facilitate selective recording of neural activity within an intact nerve. Even though five channels are illustrated in FIG. 1, it will be understood that there can be any number of channels from a single channel to the maximum number of channels that fit on an integrated circuit being used for the ultra-low noise amplifier 14.

Figure 2:
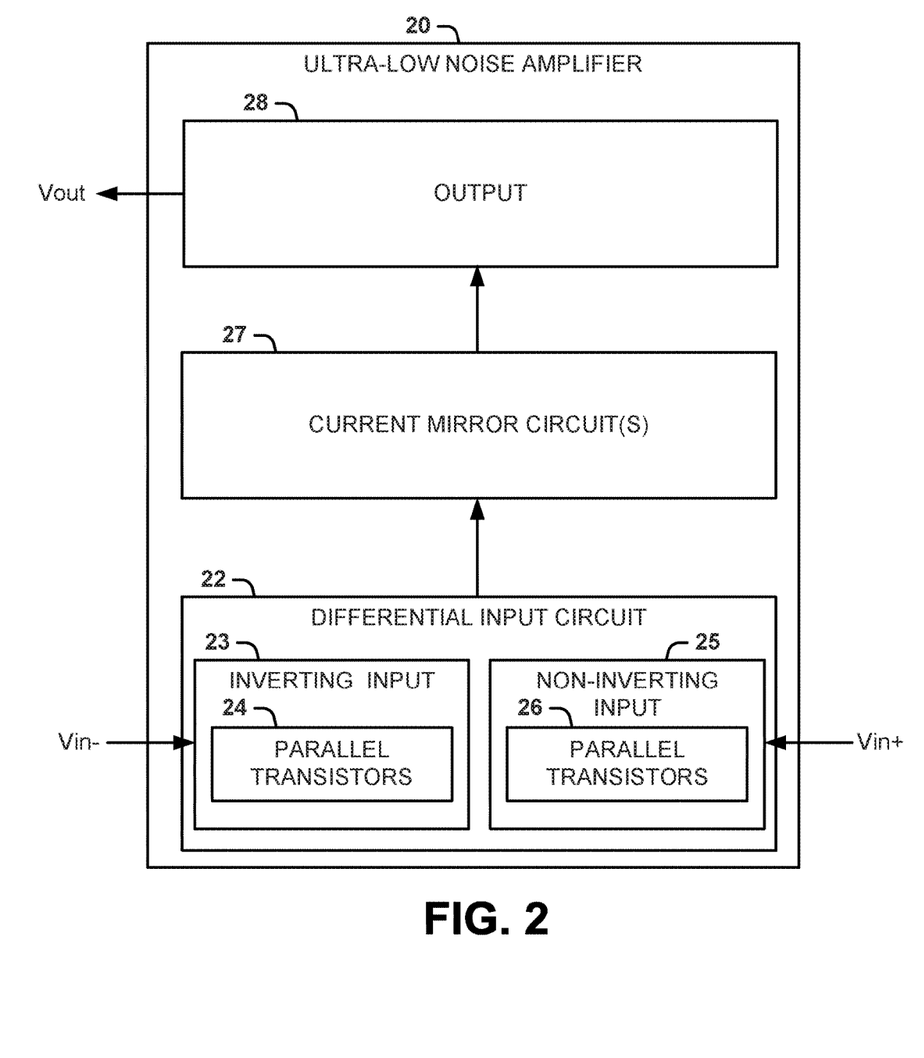
FIG. 2 is a block diagram of an example of an ultra-low noise amplifier that can be used by the system in FIG. 1.

An example of an ultra-low noise amplifier 20 is shown in FIG. 2. In this example, the ultra-low noise amplifier 20 can include a differential input circuit 22, one or more current mirror circuits 27, and an output 28. The differential input circuit 22 can include an inverting input 23 and a non-inverting input 25. The inverting input 23 receives an inverting input voltage (Vin−), while the non-inverting input voltage (Vin+).

Each of the inverting input 23 and the non-inverting input includes a plurality of parallel transistors 24, 26. For example, the plurality of parallel transistors 24, 26 can each be CMOS transistors. The plurality of parallel transistors 24, 26 can facilitate a reduction of a total noise of the ultra-low noise amplifier 20. For example, the total noise can be reduced by enlarging an equivalent input transconductance of the differential input circuit. Indeed, an amount of the total noise reduced can be reduced proportional to the square root of the number of parallel transistors 24, 26. In some instances, the non-inverting input 25 can mirror the inverting input 23 (or vice versa) with the same number of parallel transistors. For example, each plurality of parallel transistors 24, 26 can have a number greater than or equal to two parallel transistors. In another example, each plurality of parallel transistors 24, 26 can have a number greater than or equal to three parallel transistors. In yet another example, each plurality of parallel transistors 24, 26 can have a number greater than or equal to four parallel transistors. In another example, each plurality of parallel transistors 24, 26 can have a number greater than or equal to nine parallel transistors. Additionally, the plurality of parallel transistors 24, 26 can facilitate the high channel count on a single silicon wafer.

One of the current mirror circuits 27 can be coupled to the differential input circuit 22. For example, the drains of each of the plurality of parallel transistors 24 or 26 can be coupled to a respective current mirror circuit 27. For example, the current mirror circuit 27 can include at least one mirrored transistor corresponding to each of the inverting input 23 and the non-inverting input 25. In some instances, the current mirror circuit 27 can be biased based on a number of the plurality of parallel transistors 24, 26 and a biasing current value. For example, the biasing can keep the drain current the same by increasing the current mirror biasing of at least one of the current mirror circuits 27 by a multiple equivalent to the number of the parallel transistors 24, 26.

The output 28 can be coupled to an output of the current mirror circuit 27. For example, when the current mirror circuit 27 includes transistors, the output 28 can be coupled to drains of at least two of the transistors of the current mirror circuit 27 (e.g., drains of mirrored transistors). The output 28 can provide an amplified output voltage (Vout). In some instances, Vout can be based on a current difference between the plurality of parallel transistors 24 and the mirrored plurality of parallel transistors 26.

Figure 3:
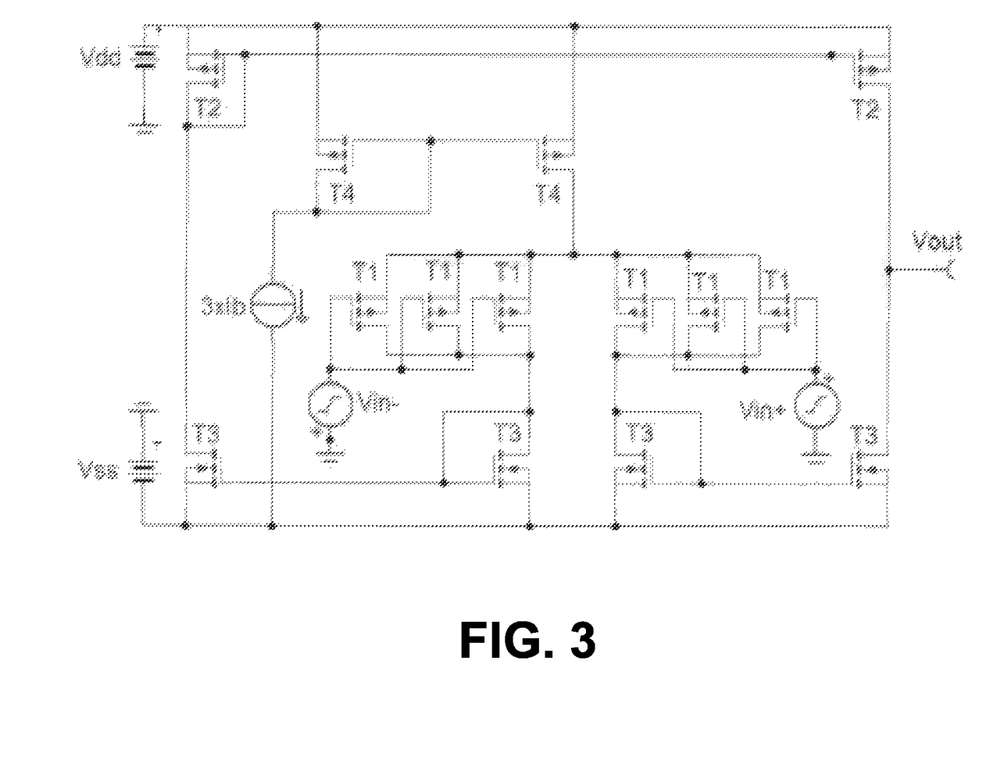
FIG. 3 an example operational transconductance amplifier (OTA) that can be used by the system of FIG. 1.

FIG. 3 shows a schematic circuit diagram of an example ultra-low noise amplifier that is a CMOS operational transconductance amplifier (OTA). This diagram (as well as a comparison to the prior art) is shown and described in U.S. Provisional Patent Ser. No. 62/337,445, the contents of which are incorporated herein by reference. Indeed, the Provisional provides a derivation of the total noise of the OTA design and its reduction with the parallel input transistors.

The example design shown in FIG. 3 has three input transistors (T1) at both the inverting input (Vin−) and the non-inverting input (Vin+). The multiple T1s increase the effective value of the input transconductance of the transistor ($g_{m1}$). Indeed, increasing T1 to 4 or 9 shows even greater benefit. In this example, the drain current for each of the T1 transistors is kept the same by increasing the T4 current mirror biasing by a multiple of the number of T1 transistors (or $3/I_b$).

Figure 4:
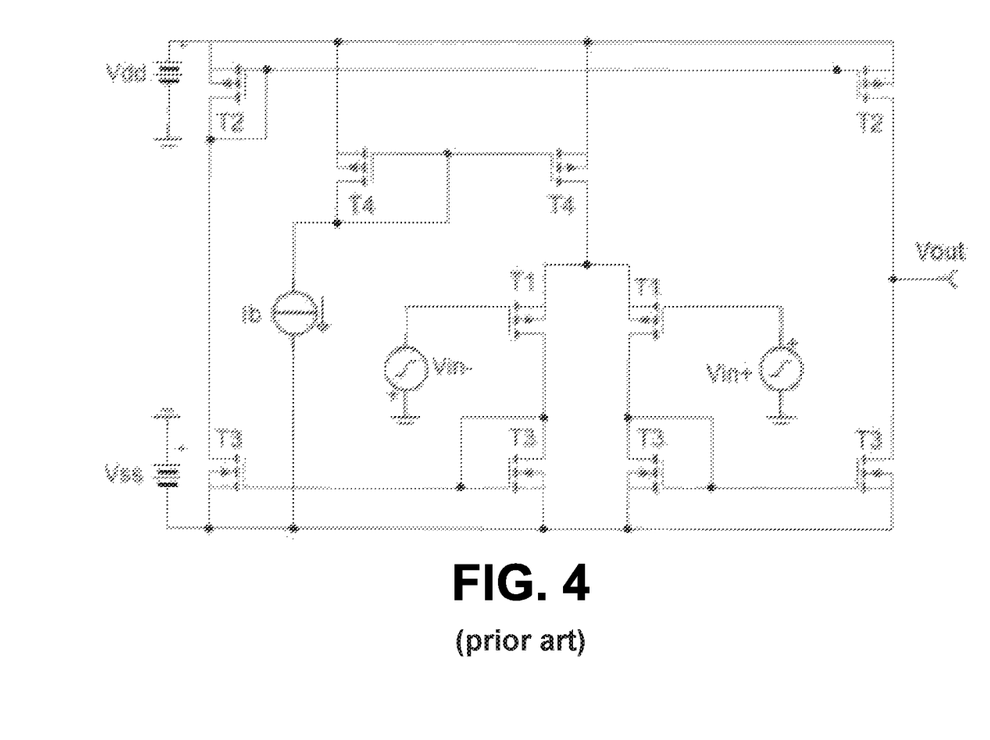
FIG. 4 is an example of a prior art OTA, which does not provide the ultra-low noise characteristics of the OTA of FIG. 3.

FIG. 4 shows an illustration of a prior art OTA with a single input transistor (T1) at the inverting input (Vin−) and the non-inverting input (Vin+). In this OTA design, the train current for T1 is set by the current source $I_b$. Sizing T1 can increase the value of $g_{m1}$ until the upper limit of $g_{m1}/I_D$ is reached. The design in FIG. 3 is superior to that shown in FIG. 4

IV. Methods

Another aspect of the present disclosure can include a method 50 (FIG. 5) for using an ultra-low noise amplifier. For example, the ultra-low noise amplifier can be used with regard to biological recordings, like neural recordings. The method 50 can be executed using the system 10 shown in FIG. 1 and described above. The ultra-low noise amplifier can provide the benefits of a low noise, low power consumption design. Advantageously, the low noise operation can enable the user of system 10 to record and amplify biological signals of a low magnitude (e.g., ~20 μV p-p), while providing an acceptable signal-to-noise ratio, and the low power consumption can reduce heat flux to living tissue surrounding the ultra-low noise amplifier when implanted. One example of an ultra-low noise amplifier is an operational transconductance amplifier (OTA), such as a CMOS OTA, which can include a plurality of parallel input transistors at a differential input of the amplifier.

Figure 5:
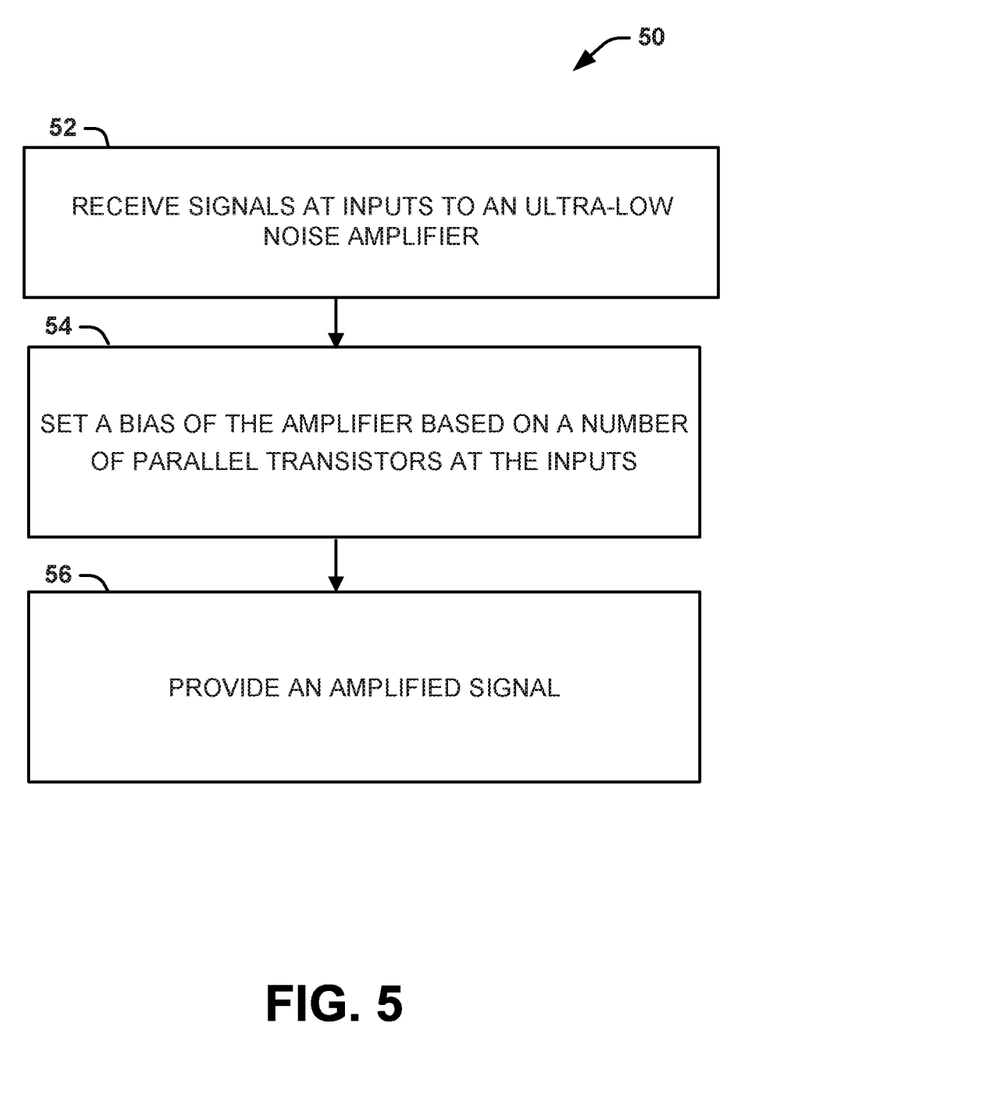
FIG. 5 is a process flow diagram illustrating a method for using an ultra-low noise amplifier according to another aspect of the present disclosure.

The method 50 can generally include the steps of: receiving signals at inputs to an ultra-low noise amplifier (Step 52); setting a bias of the amplifier based on a number of parallel transistors at the inputs (Step 54); and providing an amplified signal (Step 56). The method 50 is illustrated as process flow diagrams with flowchart illustrations. For purposes of simplicity, the method 50 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 50.

At Step 52, signals can be received at inputs to an ultra-low noise amplifier. The signals, in some instances, can include recordings by different recording devices (e.g., electrodes or electrode contacts). The inputs can be directed to different channels of the ultra-low noise amplifier. At step 54, a bias of the amplifier can be set based on a number of parallel transistors at the inputs. In other words, the bias of the amplifier for each channel can be set individually for each channel.

Previously, the only way to achieve the lowest possible voltage noise was by optimizing the geometry of the input transistor (width-to-length ratio) to increase the transconductance ($g_m$). However, the surface area of a single transistor cannot be arbitrarily increased in order to indefinitely increase $g_m$ due to the ratio between $g_m$ the and the drain current ($I_D$) being confined by an upper limit (approximately 27 $V^{-1}$). However, another way to achieve the lowest possible voltage noise, which is used by the ultra-low noise amplifier used in method 50, is by connecting a plurality of transistors in parallel at each input to increase the effective value of $g_m$ proportionally with the count of parallel input transistors and consequently to decrease the voltage noise beyond what is possible with the use of a single input transistor at each input. Another benefit of this ultra-low noise amplifier used in method 50 is that the initial operating region of the input transistors is not changed since the same value of $g_m/I_D$ is used for the individual input transistors.

At Step 56, an amplified signal (e.g., an amplified voltage signal) can be provided for further signal processing. For example, the amplified signal can be provided (through a wired connection and/or a wireless connection) to another device (e.g., a computing device with a processor and some form of non-transitory memory) for further processing. The amplified signal is often easier to process and distinguish than the originally recorded signal.

The following is claimed:

1. An apparatus comprising:
a plurality of channels each configured to receive a unique weak electrical signal from signal recording devices, wherein each of the unique weak electrical signals is a neural signal; and
an amplifier circuit comprising:
a differential input circuit configured to input the unique weak electrical signals comprising:
a number of inverting input parallel transistors to receive an inverting input voltage paired to
an equal number of non-inverting input parallel transistors to receive a non-inverting input voltage,
wherein the number and the equal number are at least four, and at least equal to another number of the plurality of channels, a current mirror circuit; and
an output configured to provide amplified weak electrical signals, wherein the amplified weak electrical signals comprise noise reduced at least by the square root of the other number of the plurality of channels.

2. The apparatus of claim 1, wherein the transistors each comprise a complimentary metal-oxide semiconductor (CMOS) transistor.

3. The apparatus of claim 1, wherein the current mirror circuit is coupled to a plurality of parallel transistor pairs and the output, and is biased based on a biasing current voltage.

4. A system comprising:
a plurality of signal recording devices, each configured to record an unique weak electrical signal, wherein each of the unique weak electrical signals is a neural signal;
an apparatus comprising:
a plurality of channels each configured to receive the unique weak electrical signal from the plurality of signal recording devices; and
an amplifier circuit comprising:
a differential input circuit configured to input the unique weak electrical signals comprising:
a number of inverting input parallel transistors to receive an inverting input voltage paired to
an equal number of non-inverting input parallel transistors to receive a non-inverting input voltage,
wherein the number and the equal number are at least four, and at least equal to another number of the plurality of channels a current mirror circuit; and
an output configured to provide amplified weak electrical signals, wherein the amplified weak electrical signals comprise noise reduced by at least the square root of the other number of the plurality of channels.

5. The system of claim 4, wherein the number of inverting input parallel transistors and the equal number of non-inverting input parallel transistors each comprise a complimentary metal-oxide semiconductor (CMOS) transistor.

* * * * *